US011074798B2

(12) United States Patent
Lee et al.

(10) Patent No.: US 11,074,798 B2
(45) Date of Patent: Jul. 27, 2021

(54) COMPUTER SYSTEM FOR ALERTING EMERGENCY SERVICES

(71) Applicant: Agency for Science, Technology and Research, Singapore (SG)

(72) Inventors: Phin Peng Lee, Singapore (SG); Thien Khanh Nguyen, Singapore (SG); Xiong Zhou, Singapore (SG); Cheryl Jia Wei Chng, Singapore (SG)

(73) Assignee: Agency for Science, Technology end Research, Singapore (SG)

( * ) Notice: Subject to any disclaimer, the term of this patent is extended or adjusted under 35 U.S.C. 154(b) by 0 days.

(21) Appl. No.: 16/345,047

(22) PCT Filed: Nov. 29, 2017

(86) PCT No.: PCT/SG2017/050587
§ 371 (c)(1),
(2) Date: Apr. 25, 2019

(87) PCT Pub. No.: WO2018/101886
PCT Pub. Date: Jun. 7, 2018

(65) Prior Publication Data
US 2019/0279480 A1   Sep. 12, 2019

Related U.S. Application Data

(60) Provisional application No. 62/428,499, filed on Nov. 30, 2016.

(51) Int. Cl.
*G08B 21/02* (2006.01)
*G10L 25/66* (2013.01)
(Continued)

(52) U.S. Cl.
CPC ............ *G08B 21/02* (2013.01); *A61B 5/0077* (2013.01); *A61B 5/1121* (2013.01);
(Continued)

(58) Field of Classification Search
None
See application file for complete search history.

(56) References Cited

U.S. PATENT DOCUMENTS 9,243,829 B1 * 1/2016 Parnell .................... F25B 45/00
10,022,545 B1 * 7/2018 Giuffrida ............. A61B 5/1124
(Continued)

FOREIGN PATENT DOCUMENTS

CN       104301570 A       1/2015
CN       104331685 A       2/2015
(Continued)

OTHER PUBLICATIONS

International Search Report and Written Opinion for PCT/SG2017/050587 dated Feb. 5, 2017, pp. 1-9.
(Continued)

*Primary Examiner* — Fekadeselassie Girma
(74) *Attorney, Agent, or Firm* — Womble Bond Dickinson (US) LLP; John J. Penny, Jr.

(57) ABSTRACT

Disclosed is a computer system for alerting emergency services. The system comprises a monitoring device, a at least one physical symptom device, a transmitter, a processor, and memory. The memory stores a predetermined baseline for one or more vital signs of a patient, a physical symptom baseline, each physical symptom baseline corresponding to a device of the physical symptom device. The memory stores instructions that cause the monitoring device to measure vital signs of the patient, compare the vital sign(s) to the respective predetermined baseline for the one or more vital signs, and if the measured vital sign(s) exceed the predetermined baseline, detect one or more physical symptoms corresponding to the physical symptom baseline The instructions cause the processor to compare the one or more physical symptoms to the respective physical symptom baseline, and initiate contact of emergency services using (Continued)

the transmitter, if at least one of physical symptoms deviates from the respective physical symptom, detect one or more physical symptoms corresponding to the physical symptom baseline. The instructions cause the processor to compare the one or more physical symptoms to the respective physical symptom baseline, and initiate contact of emergency services using the transmitter, if at least one of physical symptoms deviates from the respective physical symptom.

18 Claims, 8 Drawing Sheets

(51) Int. Cl.
  *A61B 5/00* (2006.01)
  *G08B 21/04* (2006.01)
  *A61B 5/11* (2006.01)
(52) U.S. Cl.
  CPC ............ *A61B 5/6824* (2013.01); *A61B 5/746* (2013.01); *G08B 21/043* (2013.01); *G08B 21/0453* (2013.01); *G08B 21/0476* (2013.01); *G10L 25/66* (2013.01)

(56) References Cited

U.S. PATENT DOCUMENTS

| | | | |
|---|---|---|---|
| 10,025,908 B1* | 7/2018 | Orellano | G16H 40/63 |
| 10,467,679 B1* | 11/2019 | Toumazou | A61B 5/1118 |
| 10,582,897 B2* | 3/2020 | Toumazou | G06F 1/163 |
| 10,699,806 B1* | 6/2020 | Toumazou | A61B 5/1123 |
| 10,811,140 B2* | 10/2020 | Toumazou | G16H 10/60 |
| 2003/0137900 A1* | 7/2003 | Akahane | G04F 8/08 368/110 |
| 2004/0017300 A1 | 1/2004 | Kotzin et al. | |
| 2006/0281979 A1 | 12/2006 | Kim et al. | |
| 2008/0200774 A1* | 8/2008 | Luo | A61B 5/14551 600/301 |
| 2008/0294019 A1* | 11/2008 | Tran | A61B 5/4875 600/301 |
| 2009/0005654 A1* | 1/2009 | Jung | A61B 5/121 600/300 |
| 2009/0318779 A1* | 12/2009 | Tran | A61B 5/026 600/301 |
| 2010/0160834 A1* | 6/2010 | Fong | A61B 5/1122 600/595 |
| 2011/0104642 A1* | 5/2011 | Luksch | A61C 13/0006 433/201.1 |
| 2011/0153042 A1* | 6/2011 | Burton | A63B 71/0616 700/91 |
| 2012/0189469 A1* | 7/2012 | Chou | F04B 35/01 417/321 |
| 2013/0190629 A1* | 7/2013 | Umeda | A61B 5/02225 600/479 |
| 2014/0255890 A1* | 9/2014 | Kovach | G16H 40/63 434/257 |
| 2014/0350571 A1* | 11/2014 | Maillet | A61B 34/20 606/130 |
| 2015/0068069 A1* | 3/2015 | Tran | A43B 13/183 36/136 |
| 2016/0140828 A1* | 5/2016 | DeForest | H04W 4/02 340/539.12 |
| 2016/0331255 A1* | 11/2016 | Cheatham, III | G16H 40/63 |
| 2017/0014037 A1* | 1/2017 | Coppola | A61B 5/7475 |
| 2017/0188875 A1* | 7/2017 | Banet | A61B 5/14551 |
| 2018/0029864 A1* | 2/2018 | Blackburn | B65D 25/14 |
| 2018/0140203 A1* | 5/2018 | Wang | A61B 5/369 |
| 2019/0015014 A1* | 1/2019 | Lange | A61B 5/14551 |
| 2019/0320915 A1* | 10/2019 | Gharibian | A61B 5/02108 |

FOREIGN PATENT DOCUMENTS

| | | |
|---|---|---|
| JP | 2014229199 A | 12/2014 |
| JP | 2015103116 A | 6/2015 |
| KR | 101489896 B1 | 2/2015 |
| WO | 2010/055205 A1 | 5/2010 |
| WO | 2018/101886 A1 | 6/2018 |

OTHER PUBLICATIONS

International Preliminary Report on Patentability for PCT/SG2017/050587 dated Mar. 6, 2019, pp. 1-74.

* cited by examiner

COMPUTER SYSTEM FOR ALERTING EMERGENCY SERVICES

CROSS-REFERENCE TO RELATED APPLICATIONS

This application is a U.S. National Phase Application under 35 U.S.C. 371 of International Application No. PCT/SG2017/050587, filed Nov. 29, 2017, which was published on Jun. 7, 2018 under International Publication Number WO 2018/101886, and which claims priority from U.S. Provisional Patent Application No. 62/428,499, filed on Nov. 30, 2016 and entitled "System Solution For Detection Of Symptomatic Onset Of Stroke And Alert", the entire contents of each of the foregoing patent applications are incorporated herein by reference.

TECHNICAL FIELD

The present disclosure relates to a computer system for alerting emergency services, for example, in the event of onset of stroke in a patient. The present disclosure also relates to a computer process performed by such a computer system.

BACKGROUND

Many patients are at risk of experiencing a stroke. That risk may be increased or decreased by particular lifestyle choices, pharmaceuticals, and changes in lifestyle.

For many patients, the onset of a stroke can be difficult to recognise. In some cases, a family member, friend or colleague will notice the patient is slurring their speech or is experiencing facial droop and thus alert the patient to their own symptoms. A stroke may therefore be detected some hours or even days after its onset. Late detection of a stroke can have a significant impact on the severity of conditions resulting from the stroke, such as partial paralysis and likelihood of survival.

A patient may suffer a stroke at any time. For example, a patient may suffer a stroke during their sleep or while they are away from other people who may otherwise have rendered them assistance. In such cases it can be very difficult for a patient to receive timely treatment of their condition.

It is desirable therefore to provide a system and/or computer process by which a patient can receive timely identification of their symptoms and/or by which emergency services can be notified of the potential stroke of a patient, or at least to provide a useful alternative to prior art systems and processes.

SUMMARY

In accordance with the present disclosure there is provided a computer system for alerting emergency services, comprising:
at least one monitoring device;
at least one physical symptom device, each being:
a movement sensor device;
an image capture device; or
an audio receiver device;
a transmitter;
a processor; and
memory, the memory storing:
a predetermined baseline for one or more vital signs of a patient;
at least one physical symptom baseline, each corresponding to a device of the at least one physical symptom device and being:
a predetermined baseline movement;
a predetermined baseline arrangement of facial features of the patient; or a predetermined baseline speech; and
instructions that, when executed by the processor, cause:
the at least one monitoring device to measure one or more vital signs of the patient;
the processor to compare the vital sign(s) to the respective predetermined baseline for the one or more vital signs; and
if the measured vital sign(s) exceed the predetermined baseline, detect one or more physical symptoms corresponding to the at least one physical symptom baseline, by causing:
the movement sensor device to measure a movement of one or more arms of the patient;
the image capture device to image a facial arrangement of a face of the patient; and/or
the audio receiver device to listen to a speech of the patient;
the processor to compare the one or more physical symptoms to the respective physical symptom baseline; and
initiate contact of emergency services using the transmitter, if at least one of the one or more physical symptoms deviates from the respective physical symptom baseline.

The predetermined baseline may be a predetermined baseline based on prior measurements from the patient. The prior measurements may be taken using the computer system. The processor may determine if the predetermined baseline is exceeded by determining if the respective vital sign exceeds the respective predetermined baseline by a threshold amount.

The computer system may be mounted to one of the one or more arms of the patient (the one arm). A device of the at least one physical symptom device may be a movement sensor device that directly measures an acceleration or vibration of the one arm. A device of the at least one physical symptom device may be a movement sensor device, the movement sensor device comprising an image capture device, and measuring the movement of the arm may comprise comparing positions of the arm in successive images captured by the image capture device. Measuring the movement of the arm may also, or instead, comprise identifying a position of an arm (e.g. the contralateral arm) relative to the image capture device.

A device of the at least one physical symptom device may be an image capture device, the image capture device imaging the facial arrangement by determining relative positions of two or more facial features identified from one or more images captured by the image capture device. The two or more facial features may comprise the same facial feature as represented in two images, and thus the relative position of those features is the change in position of the feature from between the two images.

A device of the at least one physical symptom device may be an audio receiver device, the audio receiver device comparing the speech to the predetermined baseline speech by identifying one or more artefacts in the speech and comparing the artefact(s) to corresponding artefact(s) in the predetermined baseline speech. For example, the audio receiver device may identify particular sharp sounds in words, such as letters "K" and "T", tone, pitch and duration, and seek to identify corresponding artefacts in a known string of text repeated by the patient when assessing whether or not their current speech is in line with, or exceeds (e.g. by a predetermined threshold amount), their baseline speech.

The processor may be configured to record in the memory a recording of the movement, facial arrangement and/or speech corresponding to the at least one physical symptom device, and the transmitter is configured to transmit the recording to a medical professional.

A computer process for alerting emergency services, comprising:
measuring one or more vital signs of a patient;
comparing the vital sign(s) to a predetermined baseline; and
if the measured vital sign(s) exceed the predetermined baseline, detecting one or more physical symptoms corresponding to at least one physical symptom baseline, by at least one of:
measuring a movement of one or more arms of the patient;
imaging a facial arrangement of a face of the patient; and/or
listening to a speech of the patient;
comparing the one or more physical symptoms to the respective physical symptom baseline; and
initiating contact of emergency services if one or more of the physical symptoms
deviates from the respective physical symptom baseline.

The predetermined baseline may be a predetermined baseline based on prior measurements from the patient. Exceeding the predetermined baseline may comprise exceeding the predetermined baseline by a threshold amount for the or each vital sign.

The computer process may be performed by a device mounted to one arm of the one or more arms of the patient (the one arm) and comprising a movement sensor device, and at least one of the one or more physical symptoms is detectable by measuring movement of the one or more arms, the movement being measured by the.

The movement sensor may comprise an acceleration or vibration sensor and measuring the movement may comprises directly measuring the movement of the one arm.

Measuring a movement of the one or more arms may comprises comparing positions of at least one of the one or more arms in successive images captured by an image capture device. Where the computer process is implemented by a computing system that is mounted to the arm of the patient, the computing system may comprise a camera or other image capture device for capturing images from which positions of the arm can be derived. In these cases, positions of the arm may be derived by comparing images of an object other than the arm, such as the body of the patient or any fixed furnishing or object in the immediate vicinity of the patient, and determining a change in position of the arm from one image to the next by determining the change in position of the image capture device with respect to the object.

At least one of the one or more physical symptoms may be detectable by imaging the facial arrangement, imaging the facial arrangement comprising capturing an image of the face of the patient from a device mounted to the one arm. Imaging the facial arrangement may instead, or in addition, comprise comparing relative positions of two or more facial features as mentioned above.

At least one of the one or more physical symptoms may be detectable by listening to a speech of the patient, and comparing the speech to a predetermined baseline speech may comprise identifying one or more artefacts in the speech and comparing the artefact(s) to corresponding artefact(s) in the predetermined baseline speech.

The computer process may further comprise providing a recording of the movement, facial arrangement and/or speech corresponding to the one or more physical symptoms to a medical professional for review.

If the measured vital sign(s) do not exceed the predetermined baseline, the computer process may involve incorporating the measured vital sign(s) into the predetermined baseline.

BRIEF DESCRIPTION OF THE DRAWINGS

Some embodiments of the present invention will now be described, by way of non-limiting example only, with reference to the accompanying drawings in which.

DETAILED DESCRIPTION

Described herein are various embodiments of a computer system and computer process for detecting onset of the symptoms of a stroke. The computer system and process may thereby detecting onset of a stroke itself. The computer system may be embodied in a smart wearable device such as a watch, wristband, ring or pair of glasses. The computer system may instead be embodied in a piece of furniture such as a bedside lamp or monitoring device. Other embodiments of the computer system comprise one or more distributed devices such as an image capture and audio receiver system positioned on a bedside table, for identifying arm movements, facial arrangement and speech of a patient, and a wrist-mounted photoplethysmogram (PPG) sensor for monitoring vital signs of a patient.

The computer system and computer process result in the monitoring and analysis of vital sign(s) and physical symptom(s) in order to detect or ascertain whether a patient is likely to be experiencing the onset of a stroke. The computer system and computer process also alert emergency services in the event that onset of a stroke has been detected or ascertained.

As used herein, the term "vital signs" will typically refer to heart rate variability (HRV) though other vital signs may be monitored such as pulse rate, respiratory rate, diastolic and/or systolic blood pressure, and temperature. It will therefore be appreciated that an appropriate sensor or device must be used to measure the relevant vital sign, such as heart rate monitor for monitoring heart rate variability and pulse rate, a movement sensor or other device for monitoring respiratory rate, a sphygmomanometer for measuring blood pressure, and a thermometer for measuring temperature.

As used herein, the term "physical symptoms" refers physical symptoms of stroke onset, such as facial drooping, speech slurring and/or arm weakness.

As used herein, the term "emergency services" refers to a party who is expected to be able to render assistance in the event that the patient experiences a stroke. Emergency services may thus include one or more of an ambulance service, a carer for a particular patient, a friend, colleague, next of kin, or any other party who is expected to be able to render assistance in the event that the patient experiences a stroke.

Figure 1:
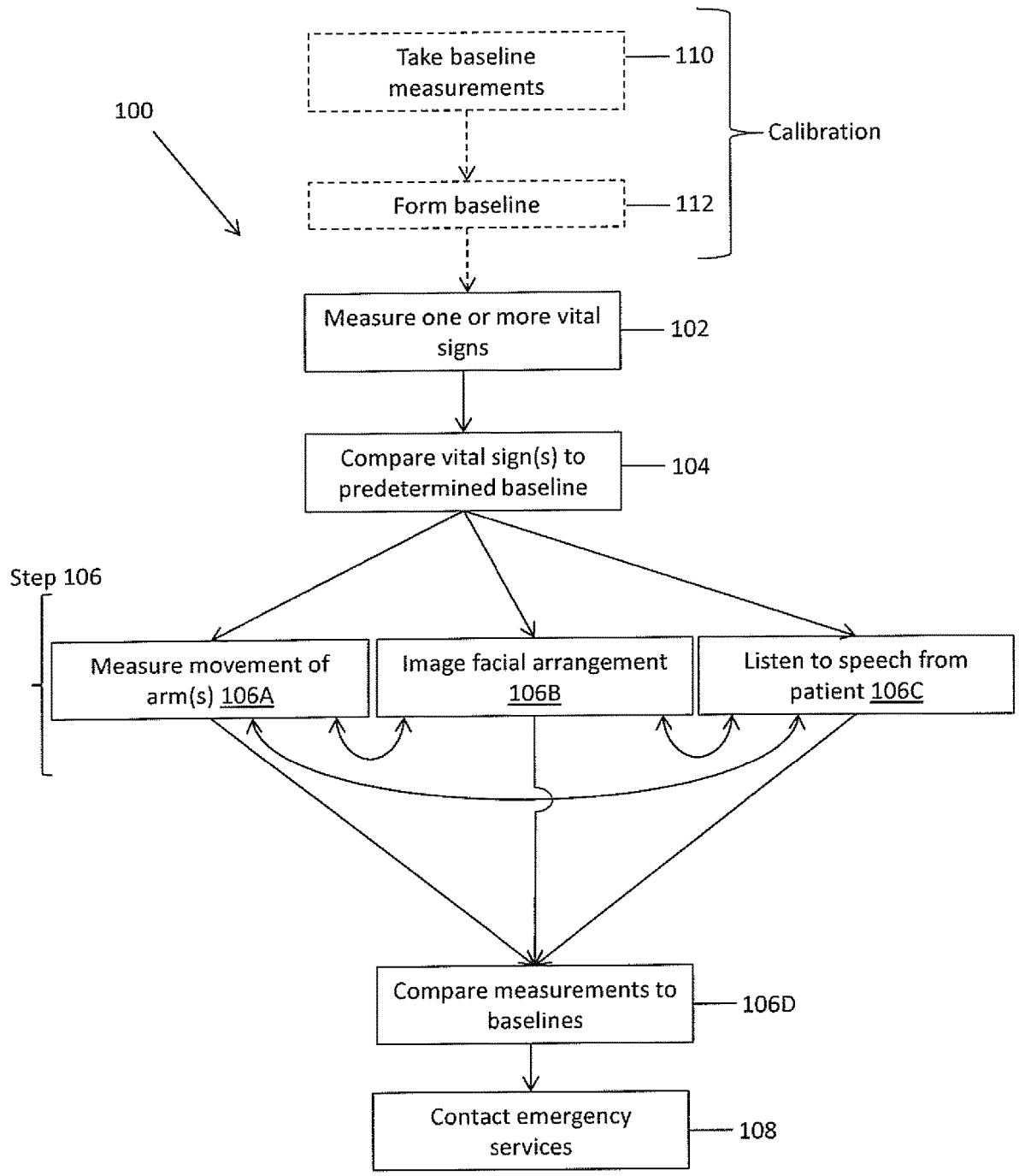
FIG. 1 illustrates a method for alerting emergency services in accordance with the present invention.

FIG. 1 illustrates a computer process 100 for alerting emergency services. The computer process 100 achieves this by firstly monitoring one or more vital signs of patient, secondly detecting physical symptoms indicating onset of a stroke, and thirdly alerting emergency services in the event that the monitoring and detecting steps indicate the onset of a stroke. The process 100 thus broadly comprises:

Step 102: measuring one or more vital signs of the patient;
Step 104: comparing the vital sign(s) to a predetermined baseline;
Step 106: assessing physical symptoms of the patient; and
Step 108: initiating contact of emergency services.

Calibration Phase

In addition to steps 102 to 108, the illustrative process 100 further comprises:

Step 110: taking baseline measurements; and
Step 112: forming a baseline from the measurements.

Steps 110 and 112 provide a calibration phase for calibrating the system 300 and the process 100 employed by such a system 300. These steps thus enable a predetermined baseline to be formed that is based on prior measurements from the patient, and is thus specific to the patient. In this context, the term "baseline" includes a normal or expected reading for the vital sign during normal activity. The term "baseline" also includes the normal or expected physical symptoms or characteristics of the patient (i.e. arm movement, facial arrangement and/or individualised speech), as will be clear from the context in which the term is used. In one example, the baseline for HRV may comprise an expected variation in HRV—which will typically be a very small variation—for normal activities such as walking, jogging, washing dishes and so forth. Similar baselines can be established for heart rate, physical fitness—which may correspond to changes in vital signs such as heart rate, HRV, blood pressure and temperature—and circadian rhythm.

During the calibration phase the system 300 monitors or measures the vital sign(s) of the patient—step 110. In one example, the system 300 comprises a wearable device mounted to a wrist of the patient. The wearable device continually measures all parameters necessary to establish the relevant baseline(s) for each vital sign.

The measurements can be processed, calibrated and fine-tuned against each other and other parameters to form one or more baselines for each vital sign—step 112. For example, when a patient is sleeping, or shortly after the patient wake up, their heart rate or pulse may be lower than the daily average for the particular patient. As the day progresses, particularly during periods of physical activity, the heart rate can be expected to be higher. Oftentimes, a patient will have a relatively consistent routine such that exercise, coffee or stimulant consumption, and relaxant consumption occurs at a particular time in the day. Thus, lower and higher baselines may be expected at relatively consistent times of day.

Measuring or monitoring one or more vital signs in accordance with Step 110, and correlating those measurements with other parameters such as time of day or relationship with other vital signs (e.g. an increase in heart rate may be accompanied by an increase in temperature where a patient undertakes physical activity), enables the baseline to be adaptive. In other words, the baseline can change over the course of a day depending on the average amount of change the patient experiences over the course of a normal day. Alternatively, different baselines may be established that are representative of, for example, the HRV of the patient at various times of day or during various activities (including inter-beat interval (IBI), HRV in the time domain and/or HRV in the frequency domain).

A threshold may then be determined for the patient. The threshold is a maximum deviation from the relevant baseline that the system 300 and process 100 will tolerate before commencing the process of checking physical symptoms for indications of the onset of a stroke—e.g. trigger the face, arms and speech (FAS) step 106 of process 100. The threshold may be very low for some vital signs such as HRV, but may be higher for other vital signs such as pulse rate. For example, HRV may have a threshold amount of ±2%, R-R interval (in the QRS complex) may have a threshold amount (e.g. standard deviation) of ±25%, blood pressure may have a threshold amount of ±10% and pulse rate may have a threshold amount of ±15% for each type of activity, or ±100% to account for differences between resting and active heart rates.

In other cases, the threshold amount may be specified as a particular maximum or minimum. For example, a maximum heart rate of 180 bpm may be set as the baseline depending on characteristics of the patient such as the age, smoker status, family history of stroke or other conditions, and other relevant considerations. The 180 bpm heart rate may be set as the baseline, and the threshold amount may be set as −100 bpm threshold amount 180 bmp, such that if heart rate exceeds the maximum heart rate, or drops below 80 bpm, Step 106 is carried out. Otherwise, Step 106 will not be triggered.

In light of the present teachings, a medical professional will appreciate the manner in which baselines and threshold amounts can be set, and which baselines and threshold amounts are appropriate for each vital sign and physical symptom of parameters such as arm movement, facial arrangement and speech.

These vital sign(s) recordings are stored in memory, which may be memory 214 within system 300, or may be another memory such as cloud storage or remote storage, or a combination thereof.

Similar baselines (i.e. physical symptom baselines) can be established for arm movement, facial arrangement and speech. For arm movement, a set of one or more arm movements may be specified. The set of arm movements may reflect a corresponding one or more arm movements that can be used to indicate whether or not the patient is experiencing the onset of a stroke—e.g. elevating an arm to a horizontal position while the patient is standing upright. The one or more movements are then recorded—step 110—and the recordings are used to form a physical symptom baseline for arm movement—step 112.

For facial arrangement, one or more images may be captured of the patient's face and various measurements taken, such as the relative positions of particular features of the patient's face (e.g. distance between corners of mouth) when the patient's face is at rest, when they are smiling and/or in various other states, along with any differences in relative positions of features when in those states (e.g. distance between each corner of the mouth when at rest compared with when smiling, or the distance between the left and right corners of the mouth and the left and right eyes respectively, when at rest and when smiling). The facial measurements are then recorded—step 110—and the recordings are used to form a physical symptom baseline for facial arrangement—step 112.

Similarly, the patient's speech may be recorded—step 110. This may involve prescribing a sequence of words, or a passage from a book, that the patient must read. Speech recognition techniques are well understood and documented. The speech recordings can then be used to form a physical symptom baseline for speech—step 112.

Figure 5:
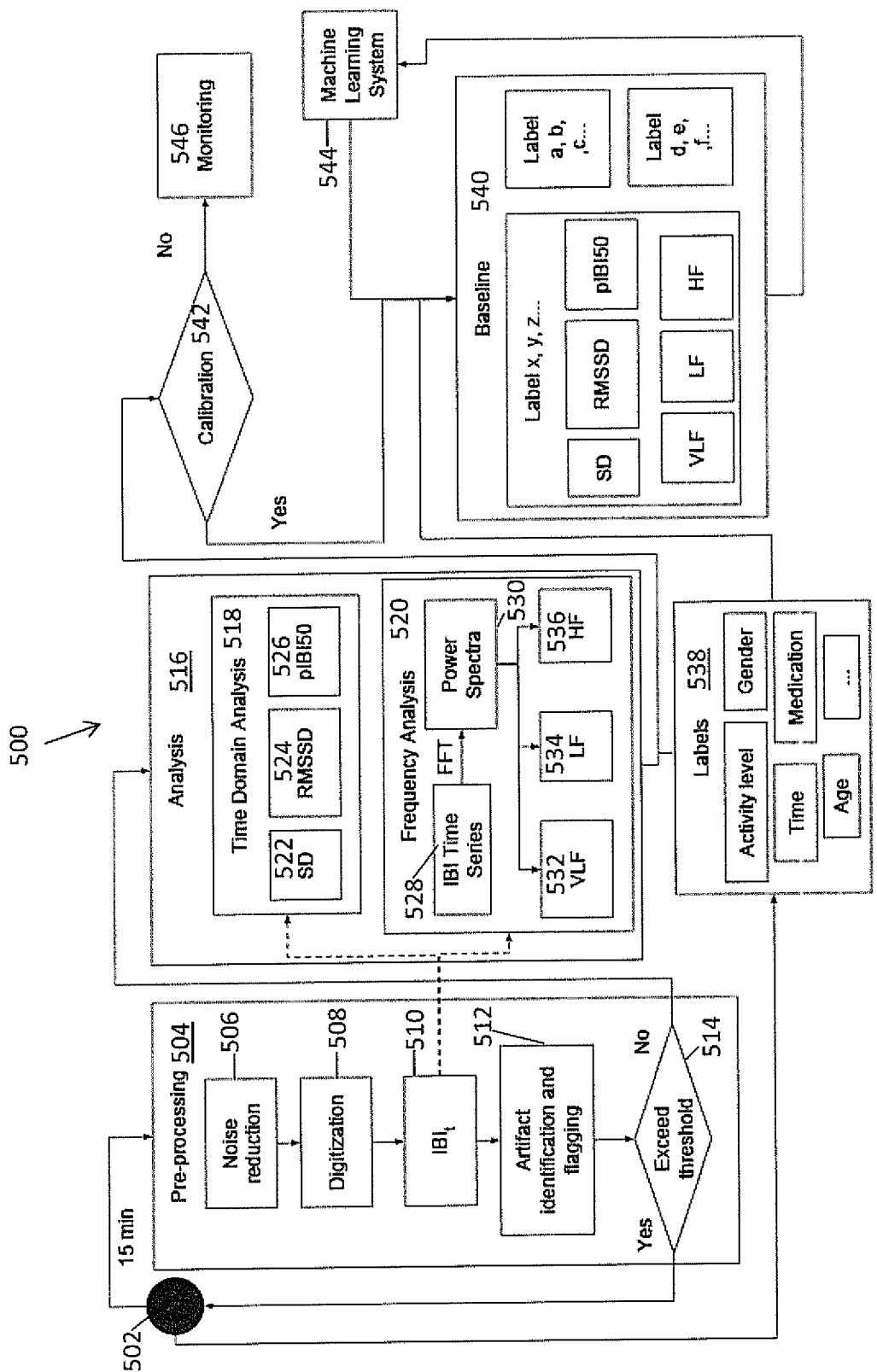
FIG. 5 illustrates a flow chart for analysis of measurements taken when forming baselines.

Analysis and calibration are discussed further with reference to FIG. 5.

Importantly, steps 110 and 112 are shown in broken lines as they are optional. Ideally, the baseline(s) is/are specific to the patient—the prior measurements from which the baseline(s) is/are formed may be made by the computer system 300 described with reference to FIG. 3. However, in some instances a baseline may be established for a group of which the patient is indicative. For example, the patient may be 46 years old, a non-smoker with low activity levels and a family history of stroke. A group of individuals from whom vital signs and physical measurements have been taken can then be used as a baseline where those individuals are, for example, non-smokers aged between 45 and 50, with low to medium levels of activity and a family history of stroke. Also, in some embodiments the baseline measurements (i.e. prior measurements used in formulating the baseline(s)) may be taken by unrelated devices and downloaded by the system 300 (e.g. from the Internet, the cloud, a physician's computer and so forth) for use in the process 100.

Assessing Measured Vital Signs Against Baseline(s)—Step 102 and Step 104

Once the baselines have been established and the process 100 and system 300 thereby calibrated, the remaining steps of process 100 can be implemented. Of these, first step to be undertaken is Step 102—measuring one or more vital signs of the patient. The measurements taken in accordance with Step 102 are then compared against a predetermined baseline—Step 104.

The manner in which vital signs are measured in accordance with Step 102 may depend on the nature of the computer system 300. For example, the computer system 300 may be embodied in a wearable device that is mounted to a wrist of the patient. At the wrist, a number of vascular lumens are close to the skin. The vascular lumens of the wrist are readily available for taking measurements of pulse and some other parameters. The wearable device can continuously monitor and analyse these vascular lumens in order to derive vital signs such as the HRV and pulse rate. Similarly, the computer system 300 may comprise a ring that measures relevant parameters resulting from movement of the finger to which the ring is attached, and resulting from vasodilation and vasoconstriction of blood vessels running along the finger to which the ring is fitted.

In some embodiments, a PPG sensor is used in the computer system 300. The PPG sensor is housed within a housing of the wearable device and is attached securely to the wrist of the patient. A contact surface of the PPG sensor directly or indirectly abuts the skin of the patient. It is desirable that an adhesive mechanism (i.e. a sticky patch or an adhesive patch, which may be a removable or replaceable adhesive patch), rather than a low friction surface-to-surface contact mechanism, be used in that attachment so that the skin of the patient at least lightly adheres to the wearable device. An adhesive mechanism provides more consistent contact across a contact area between the wearable device and skin of the patient to reduce noise resulting from variations in the amount of contact between the wearable device and skin of the patient.

Notably, some tests have shown that both horizontal and vertical motion of the wrist changes vital signs, such as HRV, detected through a PPG sensor. Similarly, bending of the wrist and rapid movements of the arms can also result in variations of vital signs measurements made using a PPG sensor and that the rest of the patient. Such changes can inadvertently result in the patient's vital signs exceeding the relevant baseline as predetermined by Step 112—i.e. a false positive is identified—and thus unnecessarily trigger Step 106.

Thus, during the calibration phase (Steps 110 and 112) the PPG sensor may derive measurements of vital signs of the patient while the patient performs various wrist movements. A sequence of analytical steps—as discussed with reference to FIG. 5—can then be used to compensate for, or filter out, data errors resulting from wrist movement. This may be achieved by correlating wrist motions and movements as detected by a movement sensor (see references 320 and 322 in FIG. 3) to changes in vital signs such as HRV where no such change is otherwise expected. For example, a patient may be asked to sit or stand still such that there should be little or no variation in HRV or pulse rate. The wearable device then measures the one or more vital signs of the patient. The patient then performs a series of arm and wrist movements, which may be prescribed by a medical professional. The wearable device measures movements of the wearable device and detects changes in the one or more vital signs, so that any such detected changes can be attributed to the movements of the wrist. The baseline, or the measurements taken at Step 102, can then be appropriately adjusted when a comparable movement is later detected to ensure the patient does not inadvertently fail Step 104, which would otherwise result in Step 106 having to be performed.

In addition, the wearable device may comprise more than one PPG sensor, or other type of sensor as used in other embodiments, so that multiple measurements for each parameter are taken and can be averaged or otherwise calibrated against each other to eliminate noise, such as noise resulting from the effect of gravity or capillary refill. Additionally, or alternatively, the sensor(s) used for vital signs measurements may be mounted on a gimbal or motorised component that is itself calibrated using data derived from the movement sensor (e.g. accelerometer) to counterbalance the effect of movement and keep the vital signs sensor(s) continuously recording from the same location on the patient's skin.

The combination of the manner of securement—e.g. adhesive—motion compensation, using an array of sensors and motion counter balance reduce noise thus reduce the likelihood that Step 106 will be unnecessarily performed.

After filtering and removing noise and errors from the measurements taken at Step 102, the one or more vital signs measured by the computer system 300 are compared to respective baselines—Step 104. To assess whether Step 106 should be performed, the computer system 300 determines whether the predetermined baseline—i.e. the baseline(s) established by Steps 110 and 112—is exceeded. While this may be a one-to-one comparison of measurements taken in accordance with Step 102 against the baseline, this will allow for no variation in the condition of a patient from day to day. It is thus preferable that Step 104 involves determining whether the predetermined baseline is exceeded by a threshold amount for each vital sign measured in accordance with Step 102. For example, a predetermined baseline for heart rate may be 70 beats per minute (bpm) and the threshold amount may be 20%, resulting in a range of 56 bpm to 84 bpm. The heart rate measured at step 102 is then compared to the baseline and predetermined threshold to see whether it falls within the range of 56 bpm to 84 bmp (inclusive) or whether it exceeds that range (i.e. falls outside the range—is less than 56 bmp or is greater than 84 bmp).

Assessing Physical Symptoms of the Patient—Step 106

After it is determined—in accordance with Step 104—that the predetermined baseline has been exceeded, the computer system 300 performs Step 106, namely an assessment of the physical symptoms of the patient. This involves at least one of:

Step 106A: measuring the movement of one or both arms of the patient;

Step 106B: imaging a facial arrangement of the patient;

Step 106C: listening to speech from the patient; and

Step 106D: comparing the measurements produced in accordance with relevant one(s) of Steps 106A, 106B and 106C against a respective physical symptom baseline, such as a predetermined baseline movement, arrangement and speech. For illustration purposes, in the embodiments described hereafter, all three of Steps 106A, 106B and 106C may be performed, though it will be understood that it may only be necessary to perform one of those steps in other embodiments of the present disclosure.

To ensure the appropriate measurements are taken by which the computer system 300 can assess the patient, instructions are delivered to the patient. The instructions advise the patient to perform the requisite arm, facial and/or speech functions that can be compared to the corresponding physical symptom baseline(s). In some instances, the computer system 300 comprises a display (see, e.g., reference 304 of FIG. 3) that visually displays instructions to the patient. The computer system 300 may instead, or in addition, provide audio instructions via a speaker (see, e.g., reference 316 of FIG. 3). In some cases, a patient may be unaware that their vital signs measurements have been found to exceed the respective baseline, thus an audio response (e.g. audible alarm) may be used to attract attention to the computer system 300 that then presents visual instructions to the patient to facilitate performance of Steps 106A, 106B and/or 106C.

One common symptom of a stroke is weakness in the arms. Weakness in the arms is assessed according to Step 106A. To detect weakness in the arms, the patient may be prompted to lift an arm to a predetermined position. In some embodiments, such as those discussed above, the computer system 300 comprises a wearable device. The wearable device may be mounted to the arm of the patient such as at the shoulder, upper arm, elbow, for arm, wrist, hand finger (e.g. a ring). Thus movements of the device may be measured and assumed to correspond to movements of the arm (including the hand) to which the device is attached.

Motion of the arm may be detected in a variety of ways. In some embodiments, the wearable device comprises an image capture device (e.g. a camera) which may also be used to detect facial arrangement in accordance with Step 106B. Measuring a movement of the arm may thus comprise comparing positions of the arm in successive images captured by the image capture device. In these cases, positions of the arm may be derived by comparing images of an object other than the arm, such as the body of the patient, the contralateral arm, or any fixed furnishing or object in the immediate vicinity of the patient, and determining a change in position of the arm from one image to the next by determining the change in position of the image capture device with respect to the object. In other embodiments, an external device, such as a device sitting on a table, may capture images of the patient and determine the various positions of their arm between successive images.

It will often be more accurate to use a movement sensor device housed within the wearable computer system 300, than to use image capture to assess or measure arm movement. That movement sensor device may be an accelerometer or other acceleration or vibration sensor such that movement of the arm can be taken directly (i.e. derived from the movement itself rather than by inference, such as may be necessary by deriving arm movements from images).

Figure 7:
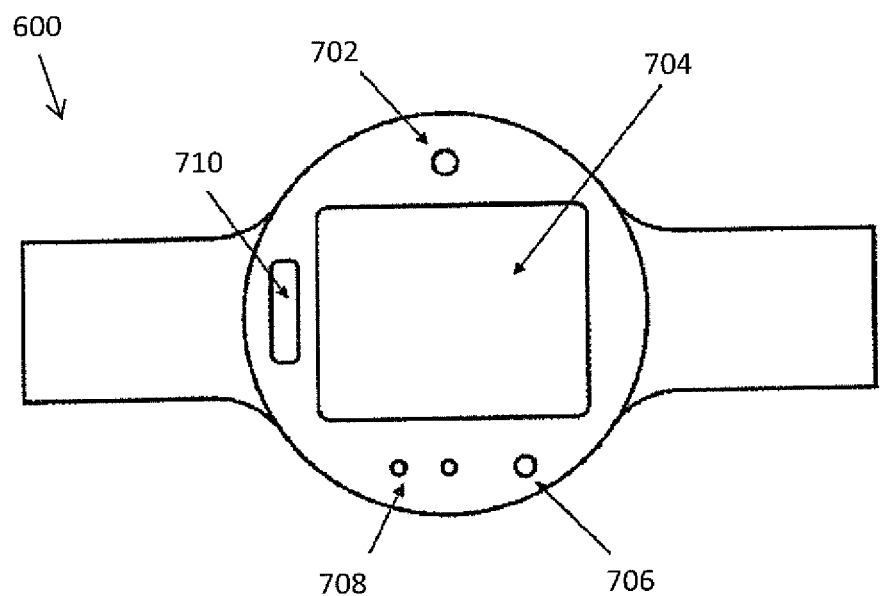

Since paralysis resulting from a stroke may not affect the side of the body to which the wearable device is attached (i.e. may not affect the arm (the one arm), of the patient's two arms, to which the device is attached), it is desirable that the patient perform the arm lifts with both arms. In some cases the arms will be moved in unison. In other cases, the arms will be moved one after the other. The wearable device may thus comprise a button (e.g. button 710 as shown in FIG. 7), so that the user must first lift one arm, then lift their second arm to the same position and press the button on the wearable device.

Figure 3:
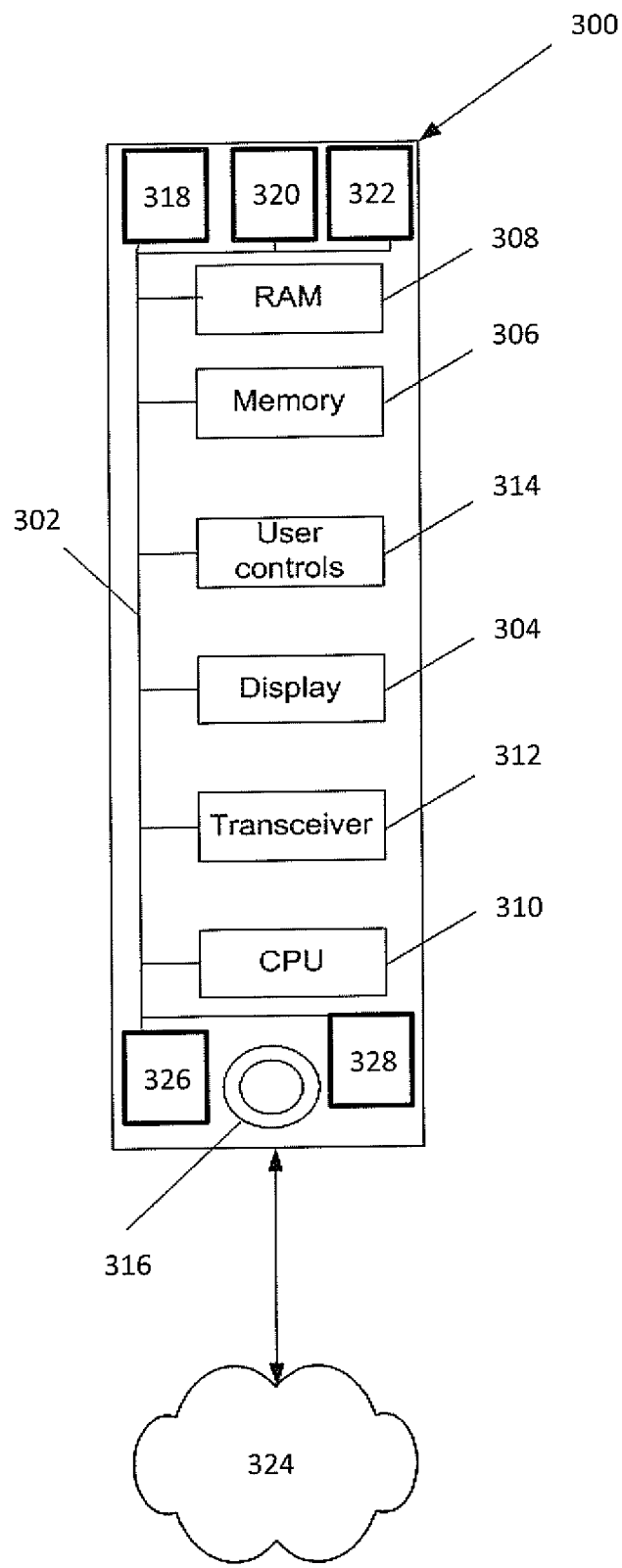
FIG. 3 illustrates a computer system for performing the processes illustrated in FIGS. 1 and 2.

A movement sensor device, such as an accelerometer, may measure the acceleration, velocity, displacement, drift (e.g. lateral drift) and position of the arm to which a wearable device comprising the movement sensor is attached. In contrast, a movement sensor comprising an image capture device, such as side camera 602 in FIG. 6, may measure these parameters for both arms. For the arm to which the computer system 300 is attached (the ipsilateral arm), the image capture device can determine its position by reference to other objects as discussed above. For the other arm (the contralateral arm) the image capture device may capture images of that arm and determine the change in position of the contralateral arm between successive images. Thus, an accelerometer or image capture device may be used to determine movement (including drift, such as lateral drift) of the ipsilateral arm, and an image capture device may also detect the position of the contralateral arm. As a result, in some embodiments, both an accelerometer and image capture device are provided. In other embodiments, only the image capture device is provided. In either of these cases, the relative positions of both arms can be detected. Moreover, movement of only one arm may be detected, or movement of both arms may be detected, as suitable in any particular application (e.g. some patient's may only have one arm).

Where an image capture device is provided, such as camera 320 in FIG. 3, the relative positions of one or both of the arms can be determined from analysing images of one arm, taken from a computing system 300 attached to the other arm. To achieve this, the image capture device 320 may be mounted at an angle from which it can see both the contralateral arm and the face, so that it can be used for both Step 106A and Step 106B. The image capture device may instead be mounted on a pivot to enable rotation about an axis. This allows the camera to rotate between a position in which it faces the contralateral arm and a position in which it is directed toward the face of the patient. The computing device 300 may instead include two image capture devices, one of which is mounted to face the contralateral arm, the other being mounted to capture the face of the patient.

The camera may comprise a visible light detection device such as a standard camera, or may comprise an ultrasound or infrared sensor, laser (e.g. laser dot) projector and receiver pair and so forth—similar comments apply to any camera described with reference to the present figures and defined in the claims. In addition, the device may comprise a separate device mounted on each arm so that image capture can be avoided for arm movement measurements or monitoring.

The computing system 300 may thus be designed to capture the movement of each arm, confirm that both arms have been moved to substantially the same position (e.g. by a button press), and the relative positions between both arms.

While there is no fixed order in which Steps 106A, 106B and/or 106C must be performed, in some embodiments where both Steps 106A and 106B are performed, Step 106A will be performed in advance of Step 106B to ensure the image capture device (see reference 320 in FIG. 3) is positioned laterally outwardly from the shoulder in order to capture an image of the face of the patient.

To image a facial arrangement of the patient in accordance with Step 106B, the system 300 may provide audio and/or visual commands (using the speaker 316 and/or display 304 of the computing system 300) to the patient. These commands may instruct the patient to provide a defined facial expression to the computing system 300, the expression being selected to make facial droop evident or otherwise to emphasise disparities between movements on one side of the face when compared with the other side of the face. For example, the patient may be asked to smile or blink.

Figure 2:
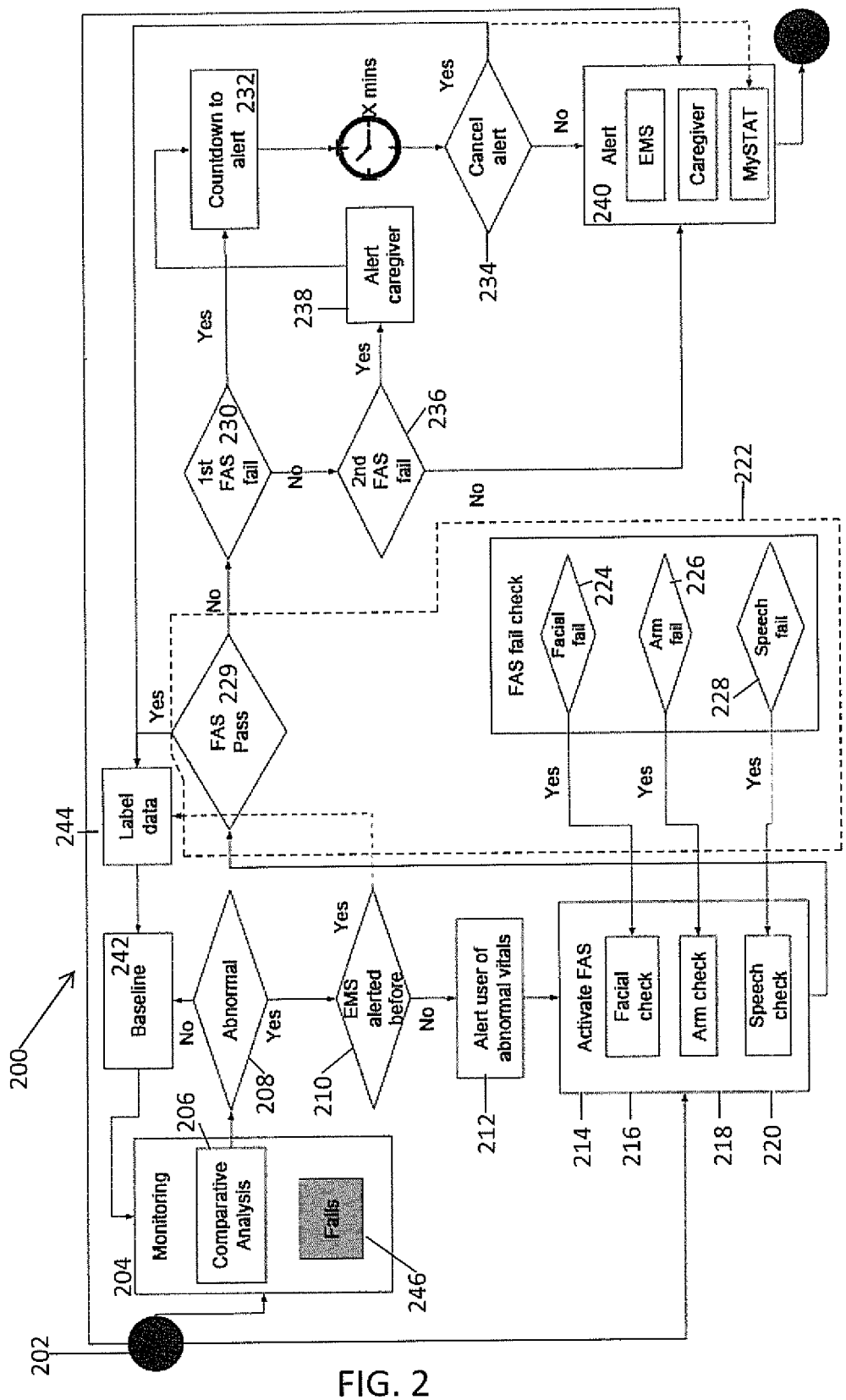
FIG. 2 is a schematic illustration of the method of FIG. 1.

The computer process 100, as discussed further with reference to FIG. 2, then images the facial arrangement of the patient—i.e. it assesses the relative positions of various facial features. This may include the position of one feature (e.g. the left corner of the mouth) with respect to another feature (e.g. the right corner of the mouth), or the relative positions of the same feature at the start and end of a facial gesture (e.g. the positions of the left corner of the mouth when a patient's mouth is in a relaxed state and when the patient's mouth is in a smiling gesture, or the positions of eyelids during a winking/blinking gesture). These features may include the positions of the lips, the corners of the mouth, the nasolabial folds, the degree of droopiness or openness of the eyelids (particularly the upper eyelids), asymmetry of the frontalis muscle, and/or movement or asymmetry of the zygomaticus minor, zygomaticus major, orbicularis oris, buccinators, levator labii superioris, levator labii superioris alqeque nasi, and/or movement or asymmetry in other features as defined by a medical professional as being potentially relevant to an assessment of the onset of a stroke. Image analysis techniques are well understood and their application will be appreciated by a skilled person in view of the present teachings.

The recitation of a line of speech need not occur at any particular time with respect to Steps 106A and 106B. If those steps are performed in the relevant embodiment. Speech may be delivered by the patient before, during or after those steps though performing speech during Step 106B may result in the arrangement of features involving position of the mouth failing to conform to the predetermined physical symptom baseline for facial arrangement. In any case, to detect the speech of the patient, the computing system 300 comprises an audio receiver—e.g. microphone or audio receiver device 318 (see FIG. 3).

The patient may be instructed to recite a predetermined phrase—e.g. using audio commands issued from speaker 316, and/or visual commands issued on display 304. The predetermined phrase may be designed to emphasise particular sounds, such as sharp "K" and "T" sounds, that are clear indicators or slurred speech when they are not pronounced correctly. The phrase may be adapted depending on the native tongue of the patient—e.g. "No ifs, ands or buts" for an English speaking patient.

The recited passage, and/or any other speech captured by the audio receiver, may be the same as that recorded during calibration Steps 110 and 112. During calibration, the recording may be received multiple times and averaged to obtain an aggregate expected sound for future recitations of the same passage when Step 106C is being performed. In addition, variations of each recording from the average may define the threshold from the predetermined physical symptom baseline for speech (i.e. the average of all recitations of the same line of speech).

Step 106C may involve detection of duration, tone, pitch and other factors that are assessed against the same factors recorded during Step 110, and used in constructing the predetermined physical symptom baseline for speech under Step 112.

Once relevant ones of the arm movement has been measured, the facial arrangement of the patient has been imaged and the speech has been received, the computer system 300 performs Step 106D—comparing the data accumulated in relevant ones of Steps 106A, 106B and 106C to respective physical symptom baselines established for those physical parameters, those physical symptom baselines having been predetermined in accordance with Steps 110 and 112. Alternatively, Step 106D may be performed after each of Steps 106A, 106B and/or 106C separately. For example, once movement of the arm(s) has been measured, that movement may be compared to the baseline for arm movement (which may include a baseline for relative arm position during and after movement of both arms). Similarly, the facial arrangement imaged at Step 106B may be compared to the relevant facial arrangement baseline at Step 106D before speech is received in accordance with Step 106C or arm movement is performed per Step 106A, or concurrently with receipt of speech or arm movement measurements.

In either case, for the arm movement to exceed a predetermined physical symptom baseline, the movement may take too long to complete, the deviation from position when complete when compared with the baseline may be too great, the lateral shift during performance of the predefined movement(s) may be too great, and so forth. For a facial arrangement to exceed a predetermined physical symptom baseline, the special relationship between features (i.e. the relative positions of those features), the time taken to complete a gesture such as a smile, or the relative starting positions of features (e.g. eyelid droop when an eye is open, when compared with the eyelid position when the eye was open during calibration) may be too far from the physical symptom baseline. Similarly, where tone, duration, pitch, sound sharpness and other factors deviate too greatly from those same quantities measured during calibration, the predetermined physical symptom baseline may be exceeded. In each of these cases, a threshold amount has been applied that dictates what is "too great" a deviation of the respective measurement from its predetermined physical symptom baseline.

Thus, Steps 106A, 106B and/or 106C, and 106D are only performed after a patient fails vital signs comparison Step 104. The same process may be repeated one or more times, for example two further repetitions—bringing the total repetitions to three—to improve confidence that the patient is indeed experiencing the onset of a stroke.

After failing to successfully complete Step 104 and/or Step 106 the computer system 300 assumes the patient is experiencing onset of a stroke and initiates contact of emergency services—Step 108—such as by sending a notification (which may include GPS coordinates of the computer system 300 and thus of the patient to which the computer system 300 is attached) to an emergency services server. That server may comprise a mobile phone telecommunications service provider server in cases where the emergency service provider is a person who is contactable by mobile phone, and that server routes the notification to the relevant mobile phone.

Emergency services may be contacted after the first failure at Step 106D, and further contacted if future performance of Steps 104 and 106D show that the first performance was a false alarm, if further repetitions are performed. In other words, emergency services may be initially notified of the potential onset of a stroke. That initial notification may then be followed up with a cancellation notification if the patient demonstrates appropriate vital signs and motor skills (i.e. arm movement, facial arrangement and speech that do not exceed the predetermined baselines) in a subsequent repetition of Steps 104 and 106D. That initial notification may instead be followed up with a confirmation in the event of a repeated failure of Steps 104 and/or 106D by the patient.

The computer system 300 may provide the location of the patient. This may be achieved by providing GPS coordinates from a GPS device housed within the computer system 300. GPS technology is well understood and need not be described in detail. GPS and other geolocation information can assist first responders to locate the patient in the event the patient has become incapacitated—e.g. the patient is unconscious. The image capture devices in the computer system 300 may also be activated to capture visual information of the stroke event.

In some embodiments discussed hereafter, emergency services may also be contacted where a severe adverse event is detected—e.g. falling or feinting of the patient. Alternatively, the patient may voluntarily contact emergency services through the device, by pressing button 328 as shown in FIG. 3.

The steps broadly described with reference to FIG. 1 are shown schematically in FIG. 2. At step 202, the process initiates. Initiating may simply comprise switching on the computer system 300 such that it can monitor vital signs. Typically, any baselines will be predetermined in accordance with steps 110 and 112, in advance of performing step 202.

Box 204 provides a continuous monitoring phase. During the monitoring phase, one or more vital signs are monitored—step 206. Monitoring vital sign(s) is discussed with reference to step 102 of FIG. 1. Measurements of vital sign(s) may be taken over prescribed intervals. For example, pulse readings may be collected in 15 minute intervals during normal monitoring conditions.

Measurements are then compared against respective baseline(s) for each vital sign to determine if there are any abnormalities—i.e. that the measurements indicate that the patient's vital sign(s) has exceeded the predetermined baseline(s)—step 208. This comparison step is discussed with reference to step 104 of FIG. 1.

If the measurements of the one or more vital signs do not exceed the relevant baseline(s) then the computer system 300 does nothing except continue to monitor the patient in accordance with step 206. If the measurements of at least one of the one or more vital signs do exceed the relevant baseline(s) then the computer system 300 checks whether emergency services have been alerted (step 210). If the answer to decision step 210 is that emergency services have been alerted, it means that at least one vital sign has recently exceeded its baseline(s), the patient has failed steps 214 and 222 (discussed below) once or twice, and the current monitoring steps are simply to record the improvement or degradation in condition of the patient.

If emergency services have not yet been alerted, it means that the present vital signs measurement is either the first or second measurement to exceed its baseline(s). The user is thus alerted of the problem—in the event that the present failure is the first failure—or repeated problem—in the event the present failure is a second failure (step 212). Alerting the user may comprise providing an audible output using speaker 316, advising the user of the vital sign for which an abnormal measurement was taken, and/or may involve displaying information about the problem on display 304. In other embodiments, step 210 is instead performed after the patient has performed one or more repetitions of the actions directed in accordance with step 106. In addition, by simply directing the patient to perform the actions required under step 106, the patient will be alerted that one or more of their vital signs exceeded the relevant baseline.

Once it is determined that a vital sign has exceeded the relevant baseline(s), the computer system 300 prompts the patient to perform the physical actions necessary to assess proper motor function to assess physical symptoms—namely movement of the arms, facial arrangement and/or speech. This action is initiated under step 214 corresponding to step 106, comprising:

arm movement measurement step 216;
facial arrangement recognition step 218; and/or
speech detection step 220.

The results of steps 216, 218 and/or 220 are assessed against their respective physical symptom baselines in step 222, which corresponds to step 106D of FIG. 1. Step 222 presently comprises:

arm movement to baseline comparison step 224;
facial arrangement to baseline comparison step 226; and/or
speech to baseline comparison step 228; and
decision step 229.

Steps 216, 218 and 220 correspond to comparison steps 222, 224 and 226 respectively. The outputs of steps 222, 224 and 226 are used by decision step 229 with which the computer system 300 assesses whether the patient has successfully performed the appropriate arm movements (step 216 and comparison step 222), is not experiencing facial droop (step 218 and comparison step 224) and has clearly recited the prescribed line of speech (step 220 and comparison step 226). If the patient passes all three tests, or the one or more of those tests as used in any particular scenario, the computer system 300 reverts back to only monitoring vital signs.

While only a single failure identified at decision step 229 may be needed in order for emergency services to be alerted and assistance rendered, in the embodiment shown in FIG. 2 the computer system 300 requires the patient to repeat the motor skills detection tests under step 214 and assessment step 222. In particular, the computer system 300 asks whether the current failure is the first failure—step 230. If so, a timer is set—step 232—and a further repetition of steps 214 and 222 is performed after the timer expires (e.g. after 3 minutes). In other embodiments, the timer set at step 232 provides a limited period of time during which the patient has the opportunity to prevent the system from contacting emergency services by successfully completing steps 214 and 222.

If the current failure is not the first failure, the computer system 300 asks whether it is the second failure—step 236. If so, the computer system 300 alerts the caregiver—step

238—restarts or continues the timer—step 232. During countdown of the timer, or following expiry of the timer, a further repetition of steps 214 and 222 is performed. The subject or patient may also elect to cancel the alert at any time, for example by pressing a button (e.g. button 710, or another similar button tasked with the function of cancelling an alert) and/or by performing a combination of one or more physical symptom tests (e.g. taps, hand gestures, reciting lines of speech).

If the current failure is not the first or second failure, but is instead a third or further failure, the computer system 300 immediately contacts emergency services—step 240. Emergency services may comprise any of the parties previously mentioned, including a caregiver for the patient, emergency ambulance services and/or a central server for recording and/or managing such alerts. The computer system 300 may then continue monitoring vital sign(s) of the patient and/or instructing the patient to perform specified actions under step 214.

In addition to the foregoing, in the event that the patient's vital signs are normal (i.e. do not exceed the relevant predetermined baseline) as determined at step 208, the computer system 300 may incorporate the measured vital signs (i.e. the vital signs measurements) into the predetermined baseline—step 242. This allows the computer system 300 to update the baseline so that it is reflective of not only the state of the user at the time the predetermined baselines were originally defined under steps 110 and 112. This is useful where, for example, a patient has experienced a stroke event or has developed blood clots, has started using the computer system 300 but, for medical or mental reasons has stopped exercising. In such circumstances the resting heart rate and some other measurements may change over the ensuing months from commencement of use of the computer system 300. Thus the baseline can adapt to suit the current state of the patient.

The same baseline update can be made to the physical symptom baselines of the arm movement(s), facial arrangement and/or speech, at step 242. This will occur in the event that the patient successfully performs the physical tests as prescribed under step 214. In order to properly incorporate new data into the baseline data, the data is labelled—step 244. Labelling data is discussed further with reference to FIG. 5.

The computer system 300 may also record the vital sign(s) measurements and/or data representing the physical symptoms of the subject, e.g. movement of the arm(s), facial arrangement and/or speech, and provide that information to a medical professional for review. The information may be sent as a file in an email, or may be downloadable directly from the computer system 300 by the medical professional.

A schematic illustration of an embodiment of the computer system 300 is shown in FIG. 3. The computer system 300 broadly comprises the following components in electronic communication via a bus 302:

(a) a display 304;
(b) non-volatile (non-transitory) memory 306;
(c) random access memory ("RAM") 308;
(d) N processing components or processor(s) 310;
(e) a transmitter (presently embodied by transceiver component 312 that includes N transceivers);
(f) user controls 314;
(g) a speaker 316;
(h) audio receiver 318;
(i) one or more image capture devices 320;
(j) a movement sensor 322; and
(k) at least one monitoring device 326.

Measurements of vital signs and physical symptom may be uploaded to remote storage or stored in the cloud 324.

Although the components depicted in FIG. 3 represent physical components, FIG. 3 is not intended to be a hardware diagram. Thus, many of the components depicted in FIG. 3 may be realized by common constructs or distributed among additional physical components. Moreover, it is certainly contemplated that other existing and yet-to-be developed physical components and architectures may be utilized to implement the functional components described with reference to the processes of FIGS. 1 and 2.

The display 304 generally operates to provide a presentation of content to a user, and may be realized by any of a variety of displays (e.g., CRT, LCD, micro-projector and OLED displays).

In general, the non-volatile data storage 306 (also referred to as non-volatile memory) functions to store (e.g., persistently store) data and executable code. Though illustrated as a single block, memory 306 may be distributed across multiple components such as audio receiver 318, image capture device(s) 320 and movement sensor 322.

In some embodiments for example, the non-volatile memory 306 includes bootloader code, modem software, operating system code, file system code, and code to facilitate the implementation components, well known to those of ordinary skill in the art, which are not depicted nor described for simplicity.

In many implementations, the non-volatile memory 306 is realized by flash memory (e.g., NAND or NOR memory), but it is certainly contemplated that other memory types may be utilized as well. Although it may be possible to execute the code from the non-volatile memory 306, the executable code in the non-volatile memory 306 is typically loaded into RAM 308 and executed by one or more of the N processing components 310.

The N processing components 310 in connection with RAM 308 generally operate to execute the instructions stored in non-volatile memory 306. As one of ordinarily skill in the art will appreciate, the N processing components 310 may include a video processor, modem processor, DSP, graphics processing unit (GPU), and other processing components. The N processing components 310 may comprise a single component or may include multiple components, such as one or more components provided in the audio receiver 318 to facilitate analysis of audio input (i.e. speech from the patient), one or more processing components provided in the image capture device(s) 320 for analysing images (i.e. imaging the facial arrangement of the patient), and one or more processing components provided in the movement sensor device 322 to analyse images—where the movement sensor includes an image capture device, which may be an image capture device incorporated into component 320—or to analyse movements—e.g. where an accelerometers is used.

The transceiver component 312 includes N transceiver chains, which may be used for communicating with external devices via wireless networks. Each of the N transceiver chains may represent a transceiver associated with a particular communication scheme. For example, each transceiver may correspond to protocols that are specific to local area networks, cellular networks (e.g., a CDMA network, a GPRS network, a UMTS networks), and other types of communication networks.

The transceiver component 312 may operate in a standard manner, to send and receive information over network 324. Component 312 may also serve to receive firmware updates and the like.

The computer system 300 is used for alerting emergency services. With reference to the processes shown in FIGS. 1 and 2, the memory 306, 308 stores a predetermined baseline for one or more vital signs of a patient, physical symptom baselines such as a predetermined baseline movement (i.e. movement(s) for one or both arms of the patient), a predetermined baseline arrangement of facial features of the patient, and/or a predetermined baseline speech. These baselines were set in accordance with steps 110 and 112. The memory 306, 308 further stores instructions that, when executed by the processor(s) 310, cause the at least one monitoring device 326 to measure one or more vital signs of the patient as discussed with reference to step 102. The instructions further cause the processor(s) 310 to compare the vital sign(s) to the respective predetermined baseline for the one or more vital signs. If the measured vital sign(s) exceed the predetermined baseline as determined under step 104, the processor(s) cause the movement sensor device 322 to measure a movement of an arm (or both arms) of the patient, the image capture device(s) 320 to image a facial arrangement of a face of the patient, and/or the audio receiver device 318 to listen to a speech of the patient. The processor(s) 310 then compares the measured movement, facial arrangement and/or speech to the respective predetermined physical symptom baseline—e.g. baseline movement, arrangement and/or speech. In the event that one or more of the measured movement, facial arrangement and speech deviate from the respective predetermined baseline movement, arrangement and speech (i.e. exceed the relevant predetermined baseline for the movement, facial arrangement and speech respectively) the processor(s) 310 initiate contact of emergency services using the transmitter, presently embodied by transceiver component(s) 312.

It should be recognized that FIG. 3 is merely exemplary and in one or more exemplary embodiments, the functions described herein may be implemented in hardware, software, firmware, or any combination thereof. If implemented in software, the functions may be transmitted or stored as one or more instructions or code encoded on a non-transitory computer-readable medium 306. Non-transitory computer-readable medium 306 includes both computer storage medium and communication medium including any medium that facilitates transfer of a computer program from one place to another. A storage medium may be any available medium that can be accessed by a computer.

In addition to vital signs monitoring as described with reference to FIGS. 1 and 2, it is common for elderly and disabled patients to be severely injured in the event of a fall. The computer system 300 illustrated in FIG. 2 thus includes a fall detection process 246.

A fall is typically detected using an accelerometer or other movement sensor device. Since a movement sensor device, such as device 322 of FIG. 3, may be incorporated into the computer system 300, that sensor device may perform the function of detecting arm movement in accordance with step 106A, and may also detect abrupt changes in position or movement of the arm that may indicate a fall.

Figure 4:
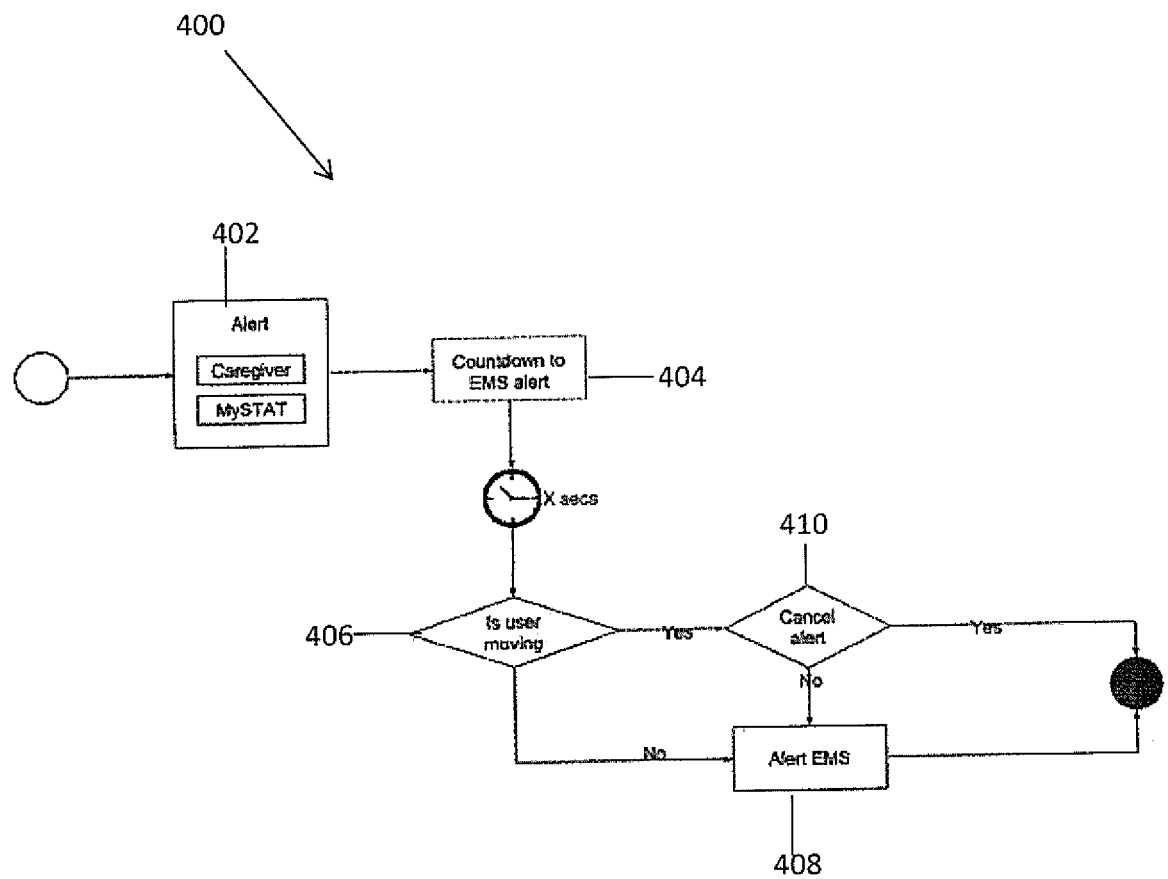
FIG. 4 illustrates a response process for responding to a detected fall.

FIG. 4 illustrates a process 400 for tending to the patient in the event of a fall. In the event that a fall has been detected, the computer system 300 alerts a caregiver (step 402) and starts a timer (step 422) at the expiry of which emergency services may be contacted. At the end of the timer period (i.e. the countdown period) the computer system 300 assesses whether the patient is moving—step 406. If the patient is not moving, emergency services are alerted—step 408. If the patient is moving, the computer system 300 determines whether the alert should be cancelled—step 410. The computer system 300 may assess the movement to determine if it is indicative of a person who is moving normally, or may combine any movement with vital signs measurements taken at step 206 to determine if there is any abnormal detectable condition. If the patient is not moving normally or vital signs indicate the patient is hurt, then emergency services are alerted 408. Otherwise, the alert is cancelled.

FIG. 5 illustrates a flow chart for analysis of measurements taken when forming baselines and monitoring. The processes will be described in broad terms since there are various suitable algorithmic and processes methodologies that may be used depending on the nature of the data desired to be extracted from measurements taken by the monitoring device 328, audio receiver device 318, image capture device (which may comprise one or more image capture devices 320) and movement sensor device 322.

The following will be discussed with reference to HRV, though other vital signs may be measured and analysed in a similar manner or as needed depending on the nature of the vital sign—e.g. blood pressure may need to be analysed differently to heart rate.

At step 502, relevant readings (i.e. measurements of the one or more vital signs) are taken. Readings may be taken at intervals, such as 15 minutes. This may involve taking a pulse reading every 15 minutes, or taking pulse readings over a 15 minutes period and sending the full 15 minutes worth of readings to the system 300.

Step 504 involves pre-processing, such as noise/error removal, band filtering, analogue to digital conversion and other steps that facilitate accurate data analysis in subsequent steps. In particular, noise reduction is performed at step 506. This may involve modifying readings in light of accelerometer or movement sensor device data that indicates the arm or wrist has moved, thus affecting measurements as discussed above. After noise reduction the measurements are digitized at step 508. For HRV measurement, digitization may involve identifying the peak-to-peak interval and labelling it an the inter-beat interval (IBI—per step 244). Each IBI is marked chronologically (step 510) and artefacts are then identified and flagged (step 512), such as changes in peak height. Artefacts in pulse readings are well understood in the art.

In cases where the baseline has been predetermined (e.g. using the steps defined in FIG. 5), and the computer system 300 is thus being used to monitor the condition of a patient, a further step will be performed to determined whether the relevant baseline(s) has been exceeded for a particular vital sign—step 514.

Analysis is then performed at step 516. This analysis take place using the noise reduced, digitized, labelled measurements in which artefacts have been identified according to step 504. Various forms of analysis are used, such as time domain analysis (step 518) and frequency analysis (step 520). For time domain analysis of the IBI labelled under step 510, the computer system 300 may identify the standard deviation (SD—step 522), the root mean square of successive difference (RMSSD—step 524) and/or the proportion of consecutive IBI that exceed a particular threshold over the average IBI measured over the 15 minute, or other, interval, e.g. 50 ms (pIBI50—step 526). For frequency domain analysis of the IBI labelled under step 510, the computer system 300 may produce an IBI time series (step 528) take a Fast Fourier transform of the IBI time series, from which a distribution of power spectra can be obtained for the IBI (step 530). From the power spectra, the high frequency (HF—step 532), low frequency (LF—step 534) and very low frequency (VLF—step 536) characteristics of the IBI can be identified.

As discussed above, there may be a single baseline for each vital sign. There may alternatively be multiple baselines for each vital sign. The baselines may change depending on time of day and other factors. To this end, the process 500 provides a labelling step 538 for labelling the results of the analysis step 516. The results or data may be labelled according to time of day, activity level (this may be derived from a combination of accelerometer data, total steps as deduced by an accelerometer or pedometer, global positioning system (GPS) location data indicating a change in location by means other than a car (i.e. at walking or riding pace), distance travelled and so forth), gender, age, pre-existing conditions or family history of particular conditions (which may include stroke), medication, mood, type of activity and so forth. This enables the computer system 300 to match particular subsequent readings to the appropriate baseline. For example, where the computer system 300 identifies the patient is jogging, the computer system 300 will assess vital signs measurements against the baseline for moderate exercise or jogging. The same can apply to physical symptom baselines.

The labelling step 538 may also assign labels to the power spectra and time domain analysis data, which may then be used as baselines against which further data from monitoring device 328 and/or devices 318, 320 and 322 can be assessed.

The range of data derived from the analysis steps 516 and labelling steps 538 may then be used to define baselines—step 540—as discussed above.

The device uses the baselines to calibrate itself—step 542. Calibration may occur once, during which all relevant baselines are made available to the computer system 300. Alternatively, to facilitate rapid processing of future vital signs measurements or arm movement, facial arrangement and/or speech measurements, the computer system 300 may decide whether it needs to calibrate itself. This may occur by the computer system 300 identifying which baseline(s) is/are relevant to the current conditions of the patient (e.g. time of day and activity level) and extract from memory (e.g. memory 306) those identified baselines as a basis for comparison step 106D and comparison step 222. If the computer system 300 determines it is loaded with the correct baseline (s), and relevant threshold amounts as determined by machine learning algorithms—step 544—the computer system 300 continues monitoring—step 546.

The baselines and any associated data (e.g. data obtained during steps 518 and 520) are then processed using a machine learning algorithm to determine threshold amounts as previously discussed—step 544. The computer system 300 is now calibrated and able to monitor vital signs—step 546.

Figure 6:
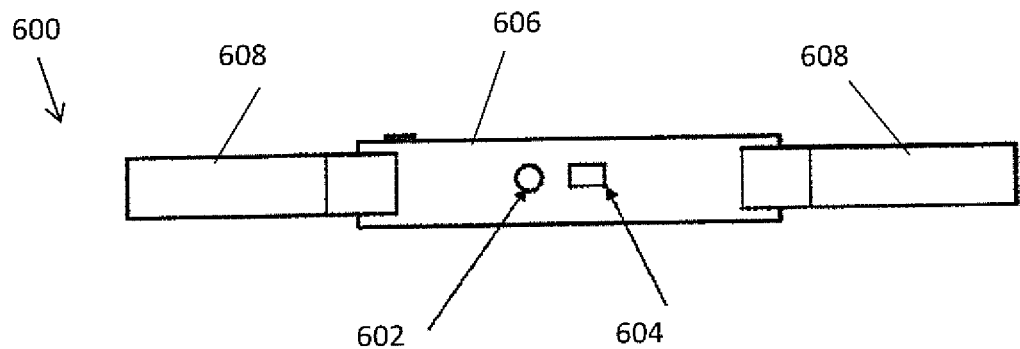
FIGS. 6 to 9 provide an embodiment of the device of FIG. 3.

FIGS. 6 to 9 illustrate how the computer system 300 may physically appear, presently in the form of a watch or ring. FIG. 6 shows a side view of a computer system 600 (being equally schematically reflected in FIG. 3), in which a side camera 602 and flash 604 are provided. As discussed above, the side camera 602 enables identification of the position of the contralateral arm relative to the position of the ipsilateral arm to which the system 600 is attached. The camera 602 may also detect facial arrangement in cases where the face 606 of the system 600 can pivot about an axis with respect to band 608 as discussed above. The flash 604 provides any necessary illumination in the event that the patient is in an area that is not well lit. The term "camera 602", and 'camera' as used elsewhere in the specification, is taken to generally describe imaging or image capture devices. As such a 'camera' may be a visible light detection device such as a standard camera, or may comprise an ultrasound or infrared sensor, laser (e.g. laser dot) projector and receiver pair and so forth FIG. 7 is a front or top view of the system or device 600, showing a camera 702, display or screen 704, microphone or audio receiver device 706, speaker 708 and button 710.

Figure 8:
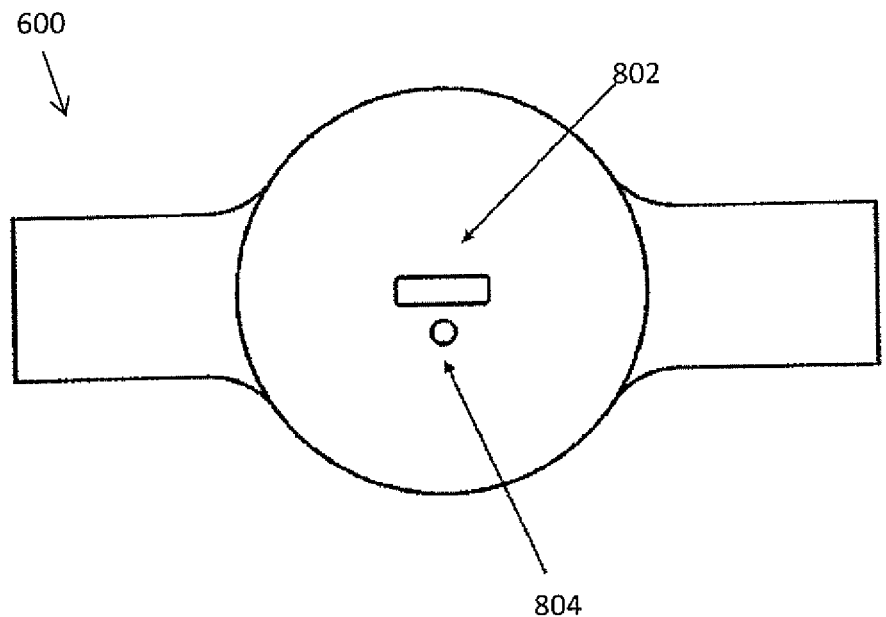

FIG. 8 shows a rear view of the system or device 600, comprising a PPG sensor. To take PPG measurements a light source is required, and a light detection device is required. To that end, system or device 600 comprises a PPG light emitting device 802 and a PPG light detection device 804, the functions of which will be understood in the art.

Figure 9:
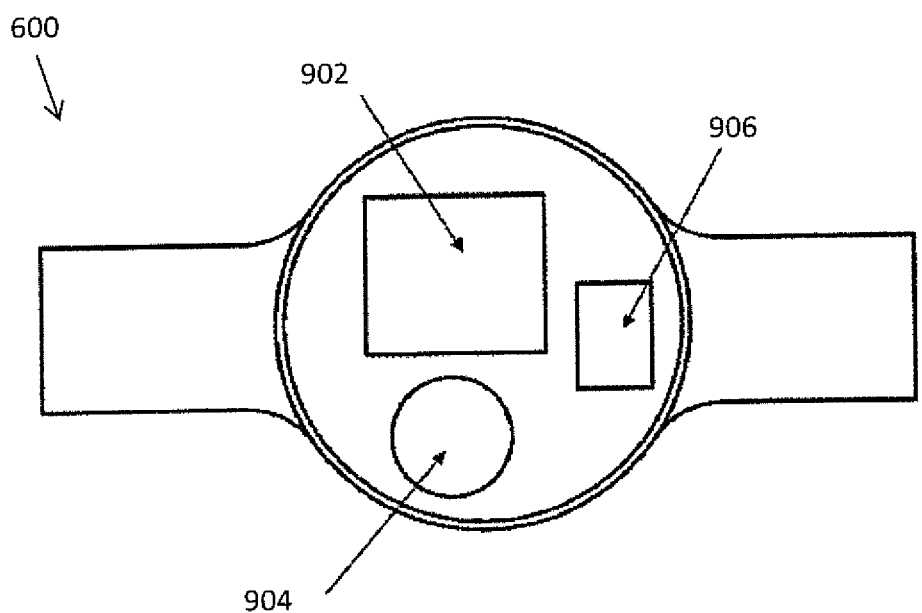

FIG. 9 provides a very high level view of a potential arrangement of internal components within the system or device 600. The components include a printed circuit board (PCB) and processor 902, a battery 905, and a further PCB associated with a GPS module, motion sensor(s) (e.g. a gyroscope or accelerometer) and a Bluetooth module for sending and receiving data using Bluetooth communication protocols (this enables recorded monitor, movement, image and speech data to be uploaded to a server or otherwise extracted by a medical professional)—906.

Figure 10:
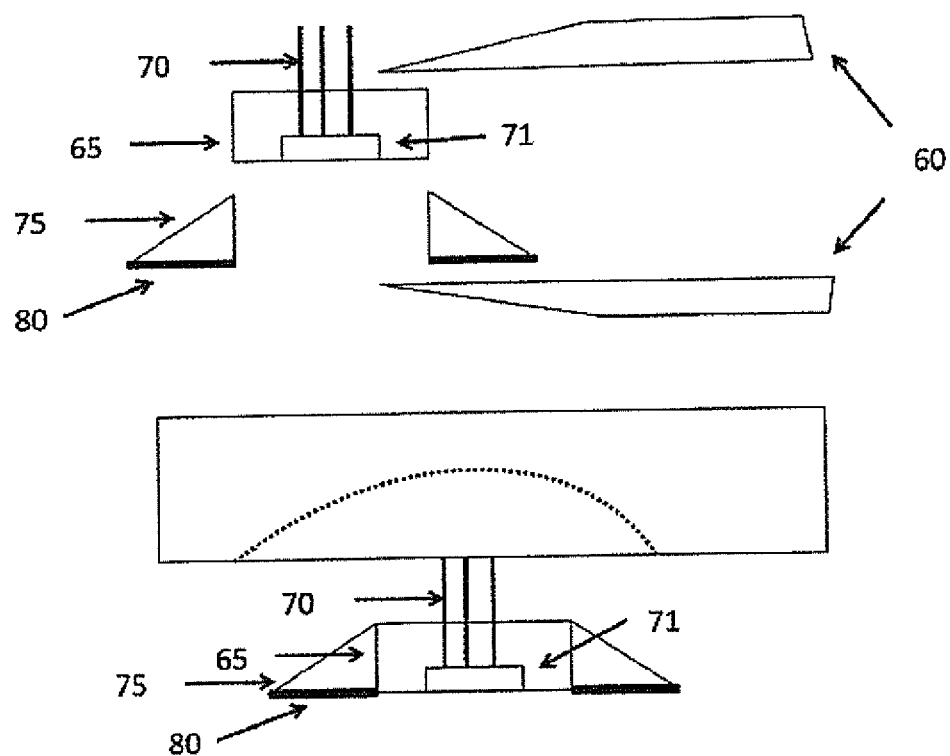
FIG. 10 illustrates a securement mechanism for the device of FIGS. 6 to 9.

FIG. 10 shows an example of assembly of a securement mechanism for a device 1000 such as that represented in FIGS. 6 to 9—e.g. how the PPG sensor may be secured to the skin via adhesive attachment. Sensor 1002 (e.g. PPG sensor with contacts 1012) is fitted into housing 1004 using tongs 1006—e.g. using a press, friction or interference fit—by insertion into recess 1010. The housing 1004 (e.g. a securement ring) provides an adhesive surface 1008 by which it can be secured to the skin of the subject, thereby positioning the sensor 1002 in a consistent position on the skin. This device 1000 can be embodiment in a watch, ring, arm band, wrist band, bracelet or any other configuration work at an appropriate position on the body of the subject.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that the prior art forms part of the common general knowledge.

The invention claimed is:

1. A computer system for alerting emergency services, comprising:
   at least on monitoring device;
   at least one physical symptom device, each being:
      a movement sensor;
      an image capture device; or
      an audio receiver device;
   a transmitter;
   a processor; and
   memory, the memory storing:
      a predetermined baseline including a normal or expected reading for the vital sign for one or more vital signs of a user during normal activity;
      at least one physical symptom baseline, each corresponding to a device of the at least on physical symptom device and being:
         a predetermined baseline movement for one or more arms of the user;

a predetermined baseline arrangement o facial features of the user; or a predetermined baseline speech of the user; and instructions that, when executed by the processor, cause:

the at least one monitoring device to measure one or more vital signs of the user;

the processor to compare the vital sign(s) to the respective predetermined baseline for the one or more vital signs; and if the measured one or more vital signs exceed the respective predetermined baseline, detect one or more physical symptoms corresponding to the at least one physical symptom baseline, by delivering instructions to prompt:

a movement of the one or more arms of the user;

a facial arrangement of the user; and/or a speech of the user, and causing:

the movement sensor device to measure movement of the one or more arms;

the image capture device to image the facial arrangement; and/or the audio receiver device to listen to the speech;

the processor to compare the one or more physical symptoms to the respective physical symptom baseline; and initiate contact of emergency services using the transmitter, if at least one of the one or more physical symptoms deviates from the respective physical symptom baseline, wherein the at least one physical symptom device includes the image capture device and the image capture device is attached to one arm of the user and the processor is configured to determine a relative position of another arm of the user by analyzing images of the another arm taken by the image capture device.

2. The computer system according to claim 1, wherein the processor determines if the predetermined baseline is exceeded by determining if the respective vital sign exceeds the respective predetermined baseline by a threshold amount.

3. The computer system according to claim 1, wherein the computer system is mounted to one of the one or more arms of the user.

4. The computer system according to claim 3, wherein a device of the at least one physical symptom device is a movement sensor device that directly measures an acceleration or vibration of the one arm.

5. The computer system according to claim 1, wherein a device of the at least one physical symptom device is a movement sensor device, the movement sensor device comprising an image capture device and measuring the movement of the arm comprises comparing positions of the arm in successive images captured by the image capture device.

6. The computer system according to claim 1, wherein a device of the at least one physical symptom device is an image capture device, the image capture device imaging the facial arrangement by determining relative positions of two or more facial features identified from one or more images captured by the image capture device.

7. The computer system according to claim 1, wherein a device of the at least one physical symptom device is an audio receiver device, the audio receiver device comparing the speech to the predetermined baseline speech by identifying one or more artefacts in the speech and comparing the artefact(s) to corresponding artefact(s) in the predetermined baseline speech.

8. The computer system according to claim 1, wherein the processor is configured to record in the memory a recording of the movement, facial arrangement and/or speech corresponding to the at least one physical symptom device, and the transmitter is configured to transmit the recording to a medical professional.

9. A computer process for alerting emergency services, comprising:

measuring one or more vital signs of a user;

comparing the measured one or more vital signs to a predetermined baseline including a normal or expected reading for the one or more vital signs of the user during normal activity; and if the measured one or more vital signs exceeds the predetermined baseline, detecting one or more physical symptoms corresponding to tat least one physical symptom baseline of the user, by at least one of:

measuring a movement of one or more arms of the user;

imaging a facial arrangement of a face of the user; and/or listening to a speech of the user;

comparing the one or more physical symptoms to the respective physical symptom baseline; and initiating contact of emergency services if one or more of the physical symptoms deviates from the respective physical symptom baseline, wherein the one or more physical symptoms include the movement of one or more arms of the user and measuring a movement of one or more arms of the user comprises measuring a movement of one arm of the user by analyzing images captured by an image capture device attached to another arm of the user.

10. The computer process according to claim 9, wherein exceeding the predetermined baseline comprises exceeding the predetermined baseline by a threshold amount for each of the vital signs.

11. The computer process according to claim 9, wherein the computer process is performed by a device mounted to one arm of the one or more arms of the user and comprising a movement sensor device, and at least one of the one or more physical symptoms is detectable by measuring movement of the one arm, the movement being measured by the movement sensor device.

12. The computer process according to claim 11, wherein the movement sensor comprises an acceleration or vibration sensor and measuring the movement comprises directly measuring the movement of the one arm.

13. The computer process according to claim 9, wherein measuring a movement of the one or more arms comprises comparing positions of at least one of the one or more arms in successive images captured by an image capture device.

14. The computer process according to claim 9, wherein at least one of the one or more physical symptoms is detectable by imaging the facial arrangement, imaging the facial arrangement comprising capturing an image of the face of the user from a device mounted to one of the one or more arms of the user.

15. The computer process according to claim 9, wherein at least one of the one or more physical symptoms is detectable by imaging the facial arrangement, imaging the facial arrangement comprising comparing relative positions of two or more facial features.

16. The computer process according to claim 9, wherein at least one of the one or more physical symptoms is detectable by listening to a speech of the user, comparing the speech to a predetermined baseline speech comprising identifying one or more artefacts in the speech and comparing the artefact(s) to corresponding artefact(s) in the predetermined baseline speech.

17. The computer process according to claim 9, comprising providing a recording of the movement, facial arrangement and/or speech corresponding to the one or more physical symptoms to a medical professional for review.

18. The computer process according to claim 9, wherein, if the measured vital sign(s) do not exceed the predetermined baseline, the measured vital sign(s) are incorporated into the predetermined baseline.

* * * * *